United States Patent [19]

Köhnke

[11] 4,167,184
[45] Sep. 11, 1979

[54] LUNG-VENTING APPARATUS

[75] Inventor: Ole B. Köhnke, Lyngby, Denmark

[73] Assignee: Ruth Lea Hesse, Rungsted Kyst, Denmark

[21] Appl. No.: 865,598

[22] Filed: Dec. 28, 1977

Related U.S. Application Data

[63] Continuation-in-part of Ser. No. 614,953, Sep. 19, 1975, Pat. No. 4,071,025.

[30] Foreign Application Priority Data

Sep. 20, 1974 [SE] Sweden ............................ 7411883

[51] Int. Cl.$^2$ .................................... A61M 16/00
[52] U.S. Cl. .................. 128/145.7; 137/843; 251/367
[58] Field of Search ............... 128/145.5–145.8, 128/142.2, 146.5; 137/525, 843; 251/367

[56] References Cited

U.S. PATENT DOCUMENTS

| 1,157,655 | 10/1915 | Mayer et al. | 128/145.7 |
| 2,428,451 | 10/1947 | Emerson | 128/145.7 |
| 2,902,992 | 9/1959 | Renvall | 128/145.7 |
| 3,083,707 | 4/1963 | Seeler | 128/145.8 |
| 3,106,204 | 10/1963 | Paramelle | 128/145.7 |
| 3,262,446 | 7/1966 | Stoner | 128/145.7 |
| 3,633,605 | 1/1972 | Smith | 137/525 |

FOREIGN PATENT DOCUMENTS 1256024 2/1961 France ............................ 128/145.7

Primary Examiner—Henry J. Recla
Attorney, Agent, or Firm—Spencer & Kaye

[57] ABSTRACT

A manually operated lung-venting apparatus includes a self-expanding bladder having a bladder inlet through which treating gas is drawn into the bladder during expansion thereof and a bladder outlet through which treating gas is driven out of the bladder during compression thereof. The apparatus further comprises a valve device having a housing attached to the bladder; and inlet chamber in the housing; a valve inlet for establishing communication between the bladder and the inlet chamber; a valve outlet which is in continuous communication with the inlet chamber and which is adapted to be connected to the respiratory system of a patient. The valve device further has a movable valve member which comprises a valve stem and a resiliently flexible, soft valve flap carried thereby and which is supported in the housing and cooperating with the valve inlet to open or close the same; and a control mechanism connected to the valve stem for moving and maintaining the movable valve stem in a closed position when the pressure in the inlet chamber exceeds a predetermined value above the ambient pressure and for moving and maintaining the valve stem in an open position when the pressure in the inlet chamber is below the predetermined value. The valve flap, in the closed position of the valve stem, readily conforms to the valve seat and, if the pressure in the inlet chamber exceeds that prevailing in the bladder, the valve flap lifts off its seat independently of the position of the valve stem.

15 Claims, 9 Drawing Figures

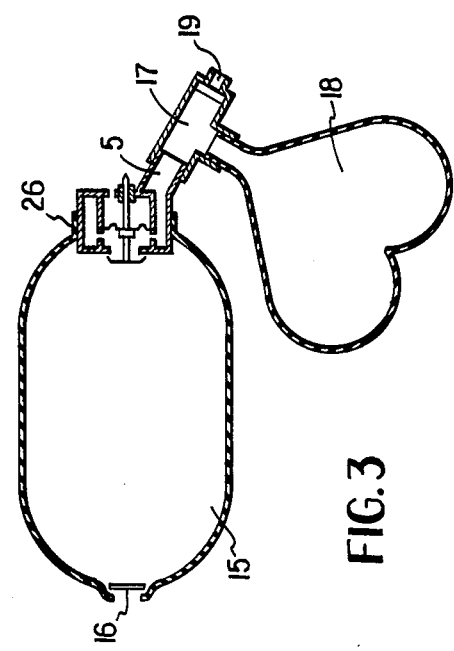
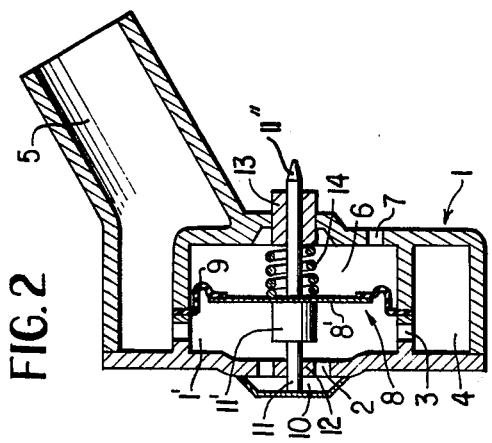
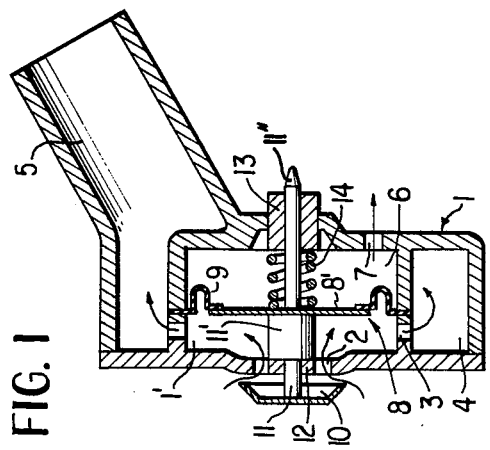
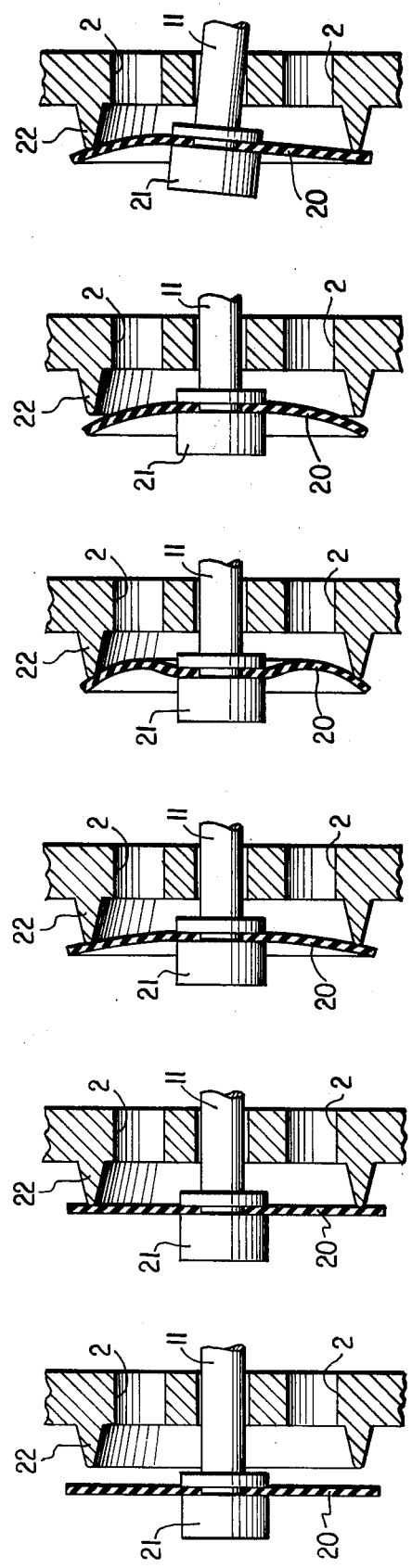

LUNG-VENTING APPARATUS

CROSS-REFERENCE TO RELATED APPLICATION

This is a continuation-in-part of application Ser. No. 614,953, filed Sept. 19, 1975 now U.S. Pat. No. 4,071,025.

BACKGROUND OF THE INVENTION

This invention relates to a manually operated lung-venting apparatus comprising a self-expanding bladder of the type having an inlet in one end wall and an outlet in the other end wall. The bladder, by periodic manual compression and release, enables breathing gas to be supplied into the lungs of a patient.

Such lung-venting systems can, in essence, belong to one of two different types, that is, open or closed systems. In the open system, the pressure source is normally a so-called self-expanding venting bladder, i.e. a bladder which after compression automatically resumes its normal shape due to its inherent resiliency. The self-expanding bladder is provided with an inlet having a one-way suction valve and an outlet in communication with a three-way breathing valve. The outlet of the breathing valve is in communication with the lungs of the patient via a breathing mask or the like. When the bladder is compressed, the suction valve is closed and the gas contained in the bladder is driven through the breathing valve and via the breathing mask into the respiratory ducts of the patient. When the bladder is released after an insufflation phase, it is refilled with fresh gas through the suction valve, while the patient is exhaling. Then a new inhalation may be performed.

Closed lung-venting systems fundamentally comprise a closed circuit through which the breathing gas is flowing in a given direction with the aid of suitable one-way valves. In this case too, a compressible venting bladder is used in order to perform the insufflation, but the bladder need not be completely self-expanding: it may be adapted to be filled, after compression, with fresh gas to some extent due to the pressure conditions prevailing in the system which is supplied with fresh breathing gas from a source of gas which is continuously connected to the system.

In these and similar lung-venting systems it is necessary to protect the lungs of the patient against excessive venting pressures while at the same time care must be taken to supply the lungs under all conditions with adequate amounts of gas. In known systems the lungs ordinarily are protected by an excess pressure valve adapted to open at a predetermined pressure value thereby to permit gas to be discharged from the system thus reducing the pressure therein.

An essential disadvantage of such systems resides in that the gas is discharged from the system when the excess pressure valve is opened which may mean that the remaining gas quantity is not sufficient to meet the patient's requirements. This condition is of particularly great importance in case the patient exhibits increased air duct resistance in front of the alveoli because the pressure drop across the air duct resistance may mean that the pressure within the system exceeds the opening pressure of the excess pressure valve before the alveoli have been sufficiently filled with gas; thus there is a great risk of an insufficient breathing-air supply to the patient.

Another disadvantage with these known systems comprising an excess pressure valve resides in that the treating gas is discharged into the environment which, on the one hand, means wastage of treating gas and, on the other hand, requires the provision of means for eliminating the discharged treating gas which may be noxious.

The problems in connection with volume losses due to discharge of the treating gas into the environment through the excess pressure valve are of particularly great importance if a self-expanding venting bladder is used for lung-venting purposes because such bladders are characterized in that only a limited maximum pumping volume is at hand, which means that volume losses cannot be compensated for by unlimited increase of the pumping volume. As such self-expanding venting bladders, in addition, are of simple construction, it is not possible to measure in a simple way the proportion of the total pumping volume actually received within the lungs of the patient in comparison with the volume of the gas escaping into the environment. Thus the evaluation of the volume received by the lungs of the patient must be made in accordance with a subjective assessment which will yield fairly accurate results only after long experience.

SUMMARY OF THE INVENTION

It is an object of the invention to provide an improved manually operated lung-venting apparatus incorporating a valve device which prevents the lungs from being exposed to harmful excess pressures while, at the same time, no treating gas is discharged into the atmosphere and which ensures that the lungs of the patient are filled with a gas volume which is exclusively determined by the lung/thorax characteristics of the patient and the predetermined control pressure but which is independent of the air duct resistance.

It is a further object of the invention to provide an improved manually operated lung-venting apparatus ensuring that the normal operating pressure of the treating gas (air) may be only slightly lower than the safety cut-off pressure thus ensuring that such operating pressure is subject only to minimum change when air is or is not supplied from the valve device to the patient.

It is still another object of the invention to provide an improved manually operated lung-venting apparatus in which the valve device ensures, in a simple and economical manner that air may flow from the valve device back to the bladder if the pressure in the latter falls below that prevailing in the valve device.

These objects and others to become apparent as the specification progresses, are accomplished by the invention, according to which, briefly stated, the manually operated lung-venting apparatus includes a self-expanding bladder having a bladder inlet through which treating gas is drawn into the bladder during expansion thereof and a bladder outlet through which treating gas is driven out of the bladder during compression thereof. The apparatus further comprises a valve device having a housing attached to the bladder; an inlet chamber in the housing; a valve inlet for establishing communication between the bladder and the inlet chamber; a valve outlet which is in continuous communication with the inlet chamber and which is adapted to be connected to the respiratory system of a patient. The valve device further has a movable valve member which comprises a valve stem and a resiliently flexible, soft valve flap carried thereby and which is supported in the housing and cooperating with the valve inlet to open or close the same; and a control mechanism connected to the valve stem for moving and maintaining the movable valve stem in a closed position when the pressure in the inlet chamber exceeds a predetermined value above the ambient pressure and for moving and maintaining the valve stem in an open position when the pressure in the inlet chamber is below the predetermined value. The valve flap, in the closed position of the valve stem, readily conforms to the valve seat and, if the pressure in the inlet chamber exceeds that prevailing in the bladder, the valve flap lifts off its seat independently of the position of the valve stem.

The closing pressure of the valve is to be chosen in such a way that the patient is not exposed to harmful excess pressures. The closing pressure may vary dependent upon the different categories of patients (adults, children, etc.). In practice the closing pressure ordinarily will be approximately 30–40 cm $H_2O$ (overpressure).

In designing the valve according to the invention it is important to avoid substantial flow resistance of the valve in the open condition thereof to ensure that the patient inhales spontaneously from the system without undue strain.

BRIEF DESCRIPTION OF THE DRAWINGS

FIGS. 1 and 2 are schematic sectional elevations of a preferred embodiment shown in an open and closed position, respectively.

FIG. 3 is a schematic sectional elevation of the same embodiment on a reduced scale, connected to a self-expanding bladder and a breathing mask.

FIGS. 4 through 9 are enlarged sectional elevations of a modification of a part of the preferred embodiment, illustrated in different operational positions.

DESCRIPTION OF THE PREFERRED EMBODIMENTS

Turning now to FIGS. 1 and 2, there is illustrated a safety valve device in an open and closed position, respectively, which is adapted to be combined, as shown in FIG. 3, with a self-expanding bladder 15 and a breathing mask 18 leading to the respiratory system of a patient. The bladder 15 is attached to the inlet side of the valve device while the breathing mask 18 is attached to the outlet side thereof.

The safety valve device comprises a housing 1 which encloses an inlet chamber 1' having one or more inlet ports 2 and one or more outlet ports 3. The housing 1 further defines an annular collecting chamber 4 which communicates with the inlet chamber 1' through the outlet ports 3. The collecting chamber 4 communicates, by virtue of a connecting nipple 5, with the breathing valve 17 which in turns leads to the respiratory system of the patient. The inlet ports 2 are, in a manner to be described later, in communication with the interior of the self-expanding bladder 15.

The valve housing 1 further encloses an additional chamber 6 which is in communication with the ambient atmospheric pressure by means of a port 7.

An airtight partition 8 separates the chambers 1' and 6 from one another. The partition 8 is movable in response to the pressure differential between chambers 1' and 6 in a direction towards or away from the inlet ports 2. Such a mobility may be accomplished in several conventional ways. In the embodiment shown, the partition 8 is formed of a rigid central plate 8' surrounded by a resilient, preferably folded portion 9 permitting the pressure-dependent mobility of the partition 8.

A movable valve member such as a valve disc 10 positioned upstream of the inlet ports 2 and cooperating therewith to open or close them dependent on the pressure conditions prevailing in the system (as it will be described in greater detail below) is connected to a valve stem 11. The latter extends from the valve disc 10 through a low-friction guide 12, the inlet chamber 1', the central plate 8' of the partition 8 and the ambient pressure chamber 6. The free terminus of the valve stem is slidably supported in a bushing 13 in the outer wall of the ambient pressure chamber 6 and terminates in a manually accessible portion 11" projecting outwardly from the bushing 13. The valve stem 11 is provided with an abutment sleeve 11' which, in the fully open position of the valve disc 10, abuts against the inner wall of the guide 12 thus limiting the stroke of the valve stem 11. The central plate 8' is sealingly attached to the valve stem 11, whereby the latter and the valve disc 10 are shifted together with the central plate 8' while the elastic portion 9 of the partition 8 undergoes a deformation. A compression spring 14 is arranged in the ambient pressure chamber 6 around the valve stem 11. One end of the spring 14 is supported by the bushing 13 while the other end of the spring 14 is in engagement with the central plate 8'. As a result, the spring 14, which is inserted in a biased state, continuously urges the valve 10 into its open position.

As it may be further observed in FIG. 3, the bladder 15 is, in a manner known by itself, provided with a one-way suction valve 16 at one end wall of the bladder, whereas the valve device according to the invention is inserted into the outlet opening 26 of the bladder 15. The nipple 5 is coupled to a conventional three-way breathing valve 17 which, in turn, is in communication with the respiratory ducts of a patient, for example, via the breathing mask 18.

The relatively rigid valve disc 10 shown in FIGS. 1 and 2 is, according to an advantageous modification of the valve structure in accordance with the invention, replaced by a readily yielding, soft, resilient valve flap 20 made of rubber or other, synthetic elastomeric material. The valve flap 20 is centrally held by a securing portion 21 at the end of the valve stem 11. The valve seat cooperating with the valve flap 20 is formed of a circular ridge 22 provided on the outer face of the front wall forming part of the housing 1. FIGS. 4 through 9 show different positions of the valve flap 20 with respect to its seat 22 in response to different pressure and operating conditions as will be described in detail hereafter.

In order to obtain the disclosed function of the valve, a valve flap 20 and the cooperating seat 22 could have the following exemplary dimensions: with a peak-to-peak diameter of 13 mm on the valve seat 22, the valve flap 20 should be approximately 15 mm in outside diameter. Silicone rubber is an excellent material for the valve flap, since the elasticity of this material remains practically constant within the temperature operating range for this type of lung-venting apparatus. With the dimensions exemplified above, the thickness of the valve flap 20 should be approximately 0.6 mm.

In the description which follows, the operation of the above-described lung-venting apparatus will be set forth.

Prior to operating the lung-venting apparatus, no pressure differential exists between chambers 1' and 6 and thus the spring 14, by urging the valve stem 11 outwardly (towards the left as viewed in the Figures), maintains the valve disc 10 (FIG. 1) or the valve flap 20 (FIG. 4) in the open position.

At the start of the operation, the valve bladder is compressed by the operator whereby the one-way suction valve 16 closes and the air is driven into the lungs of the patient through the open ports 2, the inlet chamber 1', the outlet ports 3, the annuar chamber 4, the three-way breathing valve 17 and the breathing mask 18. During this operation the pressure in the inlet chamber 1' is greater than that in the ambient pressure chamber 6, yet, during the normal inhalation phase the preset tension of the spring 14 is greater than the oppositely working pressure differential and thus the valve disc 10 is maintained open.

During normal operation, when the inhalation phase terminates and the exhalation phase begins, the three-way breathing valve 17 interrupts communication 19 between the breathing mask 18 and the bladder 15 but opens communication between the breathing mask 18 and the atmosphere. At the same time, the operator releases the self-expanding bladder 15 resulting in the opening of the one-way suction valve 16, thus filling the bladder 15 with air for performing the successive compression (inhalation) phase.

The safety valve device ensures that the pressure to which the patient's breathing organs are exposed during the assisted respiration is limited to a predetermined value. This is accomplished by causing a closure of the valve 10 when the pressure in the inlet chamber 1' reaches a maximum predetermined value or, stated differently, when the pressure differential between the inlet chamber 1' and the ambient pressure chamber 6 is capable of overcoming the force of the valve opening spring 14. It has been generally found that the maximum safe pressure is, for adult patients, approximately 30–40 cm $H_2O$. This maximum safe pressure will be referred to hereafter as the "closing pressure".

There are generally three reasons which, alone or in combination, may cause the valve device to reach the closing pressure: an excessively forceful compression of the bladder 15, an abnormally strong resistance of the breathing ducts of the patient and a high pressure in the patient's alveoli.

When the above-noted pressure differential in the chambers 1' and 6 overcomes the force of the spring 14, the valve disc 10 is pulled against its seat by the valve stem 11 as the diaphragm 8 moves towards the right in response to the differential pressure as it overcomes the force of the spring 14.

In case of the relatively rigid valve disc 10, an initial contact between the valve disc 10 and its seat surrounding the ports 2 does not ensure an immediate complete closing of the ports 2, since the force with which the valve disc 10 is then urged against its seat does not yet result in a sufficiently tight seal between the bladder 15 (undergoing compression) and the valve chamber 1'. As a result, compressed air will, although in a substantially throttled manner, still enter from the bladder 15 into the inlet chamber 1', further increasing the differential pressure and thus increasing, on the one hand, the pressure to which the patient's lung is exposed and, on the other hand, the closing pressure exerted on the valve 10. Only after an additional increase of the pressure in the inlet chamber 1' does the valve 10 sufficiently close, blocking entirely the passage of air from the bladder 15, so that no more pressure increase takes place in the inlet chamber 1'. It follows that the spring 14 should be adjusted in such a manner that the above-described additional pressure increase in the inlet chamber 1' due to the initially imperfect seal of the valve 10 is taken into consideration in determining the magnitude of the closing (cut-off) pressure.

This means that the spring 14 has to start yielding significantly before the maximum safe pressure (closing pressure) of 30–40 cm $H_2O$ is reached in the inlet chamber 1'. The practical result is that the normal operational pressure (normal insufflation pressure) has to be significantly lower than a still safe operational pressure. This circumstance unnecessarily limits the achievable maximum insufflation rate and, consequently, the operating possibilities of the lung-venting apparatus are unnecessarily limited.

In view of the above, it is a desideratum to be able to operate the lung-venting apparatus with normal insufflation pressures that are close to the closing pressure. This result is achieved by replacing the relatively rigid valve disc 10 with the relatively resiliently flexible valve flap 20 as illustrated in FIGS. 4 through 9.

During normal operation, the valve flap 20 assumes a position as shown in FIG. 4 which corresponds to the position shown in FIG. 1 for the valve disc 10.

The spring 14 is so adjusted that the valve 20 starts its closing movement (that is, the valve stem 11 starts its travel towards the right) at such a pressure in the inlet chamber 1' which is only slightly lower than the closing pressure. In response to the rightward displacement of the valve stem 11, the valve flap 20 arrives into contacting arrangement with the seat 22 as shown in FIG. 5. The pressure in the inlet chamber 1' which starts to move the valve 20 towards its seat 22 needs to be increased only slightly for achieving the valve position shown in FIG. 5 if the spring 14 is a soft spring with a strong bias. Likewise, in view of the readily conforming properties of the valve flap 20, only a very small pressure increment in the inlet chamber 1' is needed to arrive from the initial contacting position shown in FIG. 5 into the fully closed position (full sealing effect of the valve flap 20) shown in FIG. 6.

Experience has shown that a valve disc 10 (FIGS. 1 & 2), which fully seats at 30 cm $H_2O$, would have to make initial contact with its seat for a pressure in chamber 1' equal to 25 cm $H_2O$ or less. Compared to this, a valve flap 20 (FIGS. 4–9) could easily be adjusted to make initial contact as late as by 29.5 cm $H_2O$ and still make a complete seal at 30 cm $H_2O$. Since a typical ventilation would cause a pressure rise in the alveolus of approximately 15 cm $H_2O$, in the first case only 10 cm $H_2O$ is available to overcome the resistance to flow at the end of a ventilation cycle, whereas in the latter case 14.5 cm $H_2O$ is available, i.e. 45% more.

Thus, the lung-venting apparatus will operate with a greater efficiency than in case of the relatively rigid valve disc 10 because the normal operating pressure can be brought, within the safe limits, closer to the cut-off pressure than in case a valve disc 10 is used. Any further increase of the gas driving pressure, that is, a further forced compression of the bladder 15, increases the pressure differential on the two sides of the already tightly closed valve flap 20, thus increasing the force with which the valve flap 20 is forced against its seat 22. The effect of this force increase is shown in FIG. 7 which illustrates that the position of the stem 11 has not changed with respect to its position in FIG. 6; the valve flap 20, however, has become more deformed.

If the excess pressure which caused the safety valve device to close was due to an excessive insufflation pressure applied to the bladder 15 or was caused by an abnormally strong resistance encountered in the breathing duct of the patient, the pressure downstream of the valve device will drop as the gas (air) penetrates further into the air ducts and after a short time the pressure in the inlet chamber 1' will be below the closing pressure of the valve device. As a result, the spring 14 can overcome the decreased pressure differential between the inlet chamber 1' and the ambient pressure chamber 6 and as a result, the valve stem 11 will again move towards the left and assume its position shown in FIG. 1 or 4. In case the pressure in the lung alveoli of the patient equals the closing pressure, the pressure in the inlet chamber 1' cannot be reduced by introducing more air through the nipple 5 into the lungs of the patient. In the explanation that follows additional means will be described for the depressurization of the inlet chamber 1'.

As the safety valve closes, the bladder 15 will stop yielding to the operator's manual pressure, thus indicating to the operator that the closing pressure has been reached. If he then releases the bladder 15, the differential pressure between the bladder 15 and the inlet chamber 1' reverses, that is, the pressure in the inlet chamber 1' exceeds that prevailing in the bladder 15. This pressure difference will not cause an opening motion (leftward motion) of the valve stem 11; such a motion is initiated only if the pressure in the inlet chamber 1' drops with respect to the ambient pressure chamber 6. Expediently, however, the valve flap 20 is designed to be of such a resiliency that it responds immediately when the pressure differential on the two sides of the valve flap 20 reverses, that is, if the pressure in the inlet chamber 1' becomes greater than the pressure within the bladder 15 (because of the release of the external manual pressure thereon). In response to such a reversal of the differential pressure, the valve flap 20 lifts off its seat 22 solely by virtue of its resiliency, that is, without a leftward movement of the valve stem 11. Such leftward movement at that time may not be possible, because the pressure differential between the inlet chamber 1' and the ambient pressure chamber 6 has not yet changed.

A deflection of the valve flap 20 in response to a greater pressure in the inlet chamber 1' than in the bladder 15 is illustrated in FIG. 8. As a result of such an occurrence the air, in view of the reversed pressure differential, will flow back from the inlet chamber 1' through the ports 2 into the bladder 15 thus causing a pressure drop in the inlet chamber 1'. This, in turn, reduces the pressure differential between the inlet chamber 1' and the ambient pressure chamber 6 and thus the opening spring 14 will now be able to displace the valve stem to the left so that the valve will assume its open position as shown in FIG. 4.

It is seen that by providing, by virtue of the resiliency of the valve flap 20, that the pressure in the inlet chamber 1' may drop immediately upon releasing the manual pressure on the bladder 15, an opening of the valve may be achieved rapidly, independently of the breathing process of the patient. To ensure a reopening of the safety valve by providing a pressure drop in the inlet chamber 1' independently of the breathing activity of the patient is of particular importance when the lung-venting apparatus is used with patients who are about to regain own control over their breathing function, but still require some assistance. Such patients could, on their own force, generate such a pressure in the inlet chamber 1' which is greater than the insufflated pressure generated by the compression of the bladder. In such a case then the pressure in the chamber 1' would hold the spring 14 in equilibrium if the pressure in the bladder 15 is reduced, unless there is a possibility of pressure release in a backward direction (from the chamber 1' into the bladder 15) as described above in connection with FIG. 8.

Still another advantage of the valve flap 20 as compared to the relatively rigid valve disc 10 may be observed in FIG. 9. It is seen that even in case of a less than precise axial guidance of the valve stem 11, a good seal between the valve flap 20 and its seat 22 is ensured due to the pliability of the flap 20 which is capable of asymmetrical deformations. The result, among others, is a more economical structure since, at least in this respect, no narrow tolerances have to be observed.

In emergency situations (such as nerve gas injuries), the operator may want to force treating gas into the lungs of the patient even with pressures that exceed the closing pressure. In such situations, it is more important to supply the patient with sufficient amount of treating gas than to observe safety pressure limits. To achieve such a functioning of the lung-venting apparatus according to the invention, the operator may override the closing mechanism of the valve by manually pressing the projecting free end 11" of the valve stem 11 inwardly thus maintaining the valve forcibly open. This overriding mechanism may further be useful in case of a valve defeat (such as a breakage of the spring 14) which would otherwise close the valve at a pressure which is obviously too low. The projecting end 11" of the valve stem 11 further serves as a visual indicator as to the momentary position of the safety valve and the course of the patient's respiratory function.

It will be understood that the above description of the present invention is susceptible to various modifications, changes and adaptations, and the same are intended to be comprehended within the meaning and range of equivalents of the appended claims.

What is claimed is:

1. In a manually operated lung-venting apparatus including a self-expanding bladder having a bladder inlet through which treating gas is drawn into the bladder during expansion thereof; a bladder outlet through which treating gas is driven out of the bladder during compression thereof and a three-way non-rebreathing valve having an inlet in communication with the bladder outlet, a first outlet to be connected to the respiratory system of a patient, a second outlet communicating with the surrounding atmosphere and means providing one-way flow from said inlet to said first outlet and from said first outlet to said second outlet during lung ventilation; the improvement comprising, in combination, a valve device having (a) a housing attached to said bladder;
(b) means defining an inlet chamber in said housing;
(c) means defining a valve inlet in said housing; said valve inlet being connected to said bladder outlet for establishing communication between said bladder and said inlet chamber;
(d) means defining a valve outlet in said housing; said valve outlet being in continuous communication with said inlet chamber and being connected to the inlet of said three-way non-rebreathing valve;

(e) valve seat arranged on said housing and surrounding said valve inlet;

(f) a movable valve member supported in said housing adjacent said valve inlet for opening and closing said valve inlet; said movable valve member having (1) a valve stem supported in said housing in the zone of said valve inlet for longitudinal displacement through said housing in a closing direction and in an opening direction;

(2) a soft, readily deformable resilient valve flap attached to one end of said valve stem and cooperating with said valve seat; said valve flap having an open position in which it is spaced from said valve seat for maintaining communication between said bladder and said inlet chamber; said valve flap having a contacting position in which it contacts said valve seat in an undeformed state; said valve flap having a closed position in which it engages said valve seat in a deformed state; in said closed position gas flow from said bladder to said inlet chamber is fully blocked; and (g) control means responsive to pressure in said inlet chamber connected to said valve stem at a location spaced from said one end thereof for moving said valve stem in said closing direction and maintaining said valve flap in said closed position when the pressure in said inlet chamber exceeds predetermined values above the ambient pressure and for moving said valve stem in said opening direction and maintaining said valve flap in said open position when the pressure in said inlet chamber is below said predetermined values; the pressure in said inlet chamber needed for moving said valve stem into a position in which said valve flap assumes said closed position being only by a small increment larger than the pressure in said inlet chamber needed for moving said valve stem into a position in which said valve flap assumes said contacting position.

2. A lung-venting apparatus as defined in claim 1, wherein said valve flap is asymmetrically deformable for assuming said closed position when said valve stem assumes a position in which the angle defined between the length dimension of said valve stem and the direction of said longitudinal displacement is other than zero.

3. A lung-venting apparatus as defined in claim 1, wherein said valve seat is constituted by a ridge of closed course.

4. A lung-venting apparatus as defined in claim 1, wherein said valve flap is centrally attached to said valve stem.

5. A lung-venting apparatus as defined in claim 1, wherein said valve stem is provided with an abutment limiting the stroke length of said valve stem in said opening direction.

6. A lung-venting apparatus as defined in claim 1, further comprising manually operable overriding means connected to said control means for rendering said control means inoperative for maintaining said valve flap in said open position independently from the pressure in said inlet chamber.

7. A lung-venting apparatus as defined in claim 1, wherein said control means includes a movable partition wall secured to said housing and having a first face bounding said inlet chamber and an opposite, second face exposed to ambient pressure; said movable partition wall being coupled to said valve stem to move said valve stem as a function of the difference of the pressures exerted on the two faces of said movable partition wall.

8. A lung-venting apparatus as defined in claim 7, wherein said housing encloses an additional chamber in continuous communication with the ambient atmosphere; said second face of said movable partition wall bounding said additional chamber.

9. A lung-venting apparatus as defined in claim 7, wherein said partition wall comprises a stiff central plate and a surrounding resilient portion; said valve stem being attached to said stiff central plate.

10. A lung-venting apparatus as defined in claim 7, said control means further including a spring disposed within said housing and urging said valve stem in said open direction.

11. A lung-venting apparatus as defined in claim 10, said spring being constituted of a compression spring engaging said second face of said movable partition wall.

12. A lung-venting apparatus as defined in claim 10, wherein said spring has soft spring characteristics.

13. A lung-venting apparatus as defined in claim 1, said valve flap having a face oriented towards said bladder and exposed to the pressure in said bladder.

14. A lung-venting apparatus as defined in claim 1, said valve stem having a terminus projecting from said housing remotely from said valve inlet; said terminus being manually accessible to be manually operable for maintaining said valve flap in said open position independently from the pressure in said inlet chamber.

15. In a manually operated lung-venting apparatus including a self-expanding bladder having a bladder inlet through which treating gas is drawn into the bladder during expansion thereof; a bladder outlet through which treating gas is driven out of the bladder during compression thereof and a three-way non-rebreathing valve having an inlet in communication with the bladder outlet, a first outlet to be connected to the respiratory system of a patient, a second outlet communicating with the surrounding atmosphere and means providing one-way flow from said inlet to said first outlet and from said first outlet to said second outlet during lung ventilation; the improvement comprising, in combination, a valve device having (a) a housing attached to said bladder;

(b) means defining an inlet chamber in said housing;

(c) means defining a valve inlet in said housing; said valve inlet being connected to said bladder outlet for establishing communication between said bladder and said inlet chamber;

(d) means defining a valve outlet in said housing; said valve outlet being in continuous communication with said inlet chamber and being connected to the inlet of said three-way non-rebreathing valve;

(e) a valve seat arranged on said housing and surrounding said valve inlet;

(f) a movable valve member supported in said housing adjacent said valve inlet for opening and closing said valve inlet; said movable valve member having (1) a valve stem supported in said housing in the zone of said valve inlet for longitudinal displacement through said housing in a closing direction into a withdrawn position and in an opening direction into an advanced position;

(2) a soft, readily deformable resilient valve flap attached to one end of said valve stem and cooperating with said valve seat; said valve flap having an open position in which it is spaced from said valve seat for maintaining communication between said bladder and said inlet chamber and a closed position in which it engages said valve seat for fully blocking gas flow between said bladder and said inlet chamber; and (g) control means responsive to pressure in said inlet chamber connected to said valve stem at a location spaced from said one end thereof for moving said valve stem in said closing direction and maintaining said valve stem, with said valve flap, in said withdrawn position when the pressure in said inlet chamber exceeds predetermined values above the ambient pressure and for moving said valve stem in said opening direction and maintaining said valve stem in said advanced position and said valve flap in said open position when the pressure in said inlet chamber is below said predetermined values; said valve flap being in said closed position when said valve stem is in said withdrawn position and simultaneously, the force exerted on a first face of said valve flap and derived from the pressure in said bladder is at least equal to the force exerted on a second, opposite face of said valve flap and derived from the pressure in said inlet chamber; said valve flap being deformed to assume said open position in response to a greater force exerted on said second face than on said first face for allowing gas to return from said inlet chamber into said bladder through said valve inlet in said housing when said valve stem is in its said withdrawn position.

* * * * *